US00PP23756P2

(12) United States Plant Patent
Huang et al.

(10) Patent No.: US PP23,756 P2
(45) Date of Patent: Jul. 23, 2013

(54) ELM TREE NAMED 'MEIRENYU'

(50) Latin Name: *Ulmus pumila*
Varietal Denomination: Meirenyu

(75) Inventors: Yinran Huang, Shijiazhuang (CN); Junying Zhang, Shijiazhuang (CN); Jun Liu, Shijiazhuang (CN); Zongkai Jia, Shijiazhuang (CN)

(73) Assignee: Hebei Academy of Forestry Science, Shijiazhuang (CN)

( * ) Notice: Subject to any disclaimer, the term of this patent is extended or adjusted under 35 U.S.C. 154(b) by 85 days.

(21) Appl. No.: 13/374,151

(22) Filed: Dec. 14, 2011

(51) Int. Cl.
*A01H 5/00* (2006.01)

(52) U.S. Cl.
USPC ..... Plt./221

(58) Field of Classification Search
USPC ..... Plt./221
See application file for complete search history.

(56) References Cited

PUBLICATIONS

UPOV-Pluto Plant Variety Database, 2012/06, citation for 'Meirenyu'.*

* cited by examiner

*Primary Examiner* — Susan McCormick Ewoldt
(74) *Attorney, Agent, or Firm* — Penny J. Aguirre

(57) ABSTRACT

A new cultivar of *Ulmus pumila*, 'Meirenyu', characterized by its foliage that is bright yellow in color with the yellow color retained throughout the growing season on leaves with good sun exposure and by its young branches that are orange-red in color.

2 Drawing Sheets

Botanical classification: *Ulmus pumila.*
Variety denomination: 'Meirenyu'.

BACKGROUND OF THE INVENTION

The present invention relates to a new and distinct cultivar of *Ulmus pumila*, and will be referred to hereafter by its cultivar name, 'Meirenyu'. 'Meirenyu' is a new cultivar of Siberian elm, deciduous tree grown for use as a landscape plant.

The new *Ulmus* was discovered as a whole plant mutation from seeds sown of *Ulmus pumila* 'Mizhibaiyu' (not patented) in Shijiazhuang City, China in 2001.

Asexual reproduction of the new cultivar was first accomplished by one of the Inventors by grafting in 2001 in Shijiazhuang City, China. The characteristics of this cultivar have been determined to be stable and are reproduced true to type in successive generations.

SUMMARY OF THE INVENTION

The following traits have been repeatedly observed and represent the characteristics of the new cultivar as observed on seven year-old plants in Shijiazhuang City, China. These attributes in combination distinguish 'Meirenyu' as a unique cultivar of *Ulmus.*

1. 'Meirenyu' exhibits foliage that is yellow in color from leaf emergence to late May with the yellow color retained throughout the growing season on the outer leaves with good sun exposure.
2. 'Meirenyu' exhibits young branches that are orange-red in color.
3. 'Meirenyu' exhibits an upright habit with an elliptic-shaped canopy.

The parent plant, 'Mizhibaiyu' differs from 'Meirenyu' in having green leaves and in having young branches that are brown in color. 'Meirenyu' can be most closely compared to the cultivar 'Aurea' (syn. 'Beijing Gold'), not patented. 'Aurea' is similar to 'Meirenyu' in having yellow foliage and young branches that are orange-red in color. 'Aurea' differs from 'Meirenyu' in having a dwarf and more narrow plant habit.

BRIEF DESCRIPTION OF THE DRAWING

The accompanying colored photographs of 'Meirenyu' illustrate the overall appearance and distinct characteristics of the new *Ulmus*. The photographs in FIG. 1, FIG. 2, and FIG. 3 were taken of a plant seven years in age as grown outdoors in a field-plot in Shijiazhuang City, China.

Figure 1:
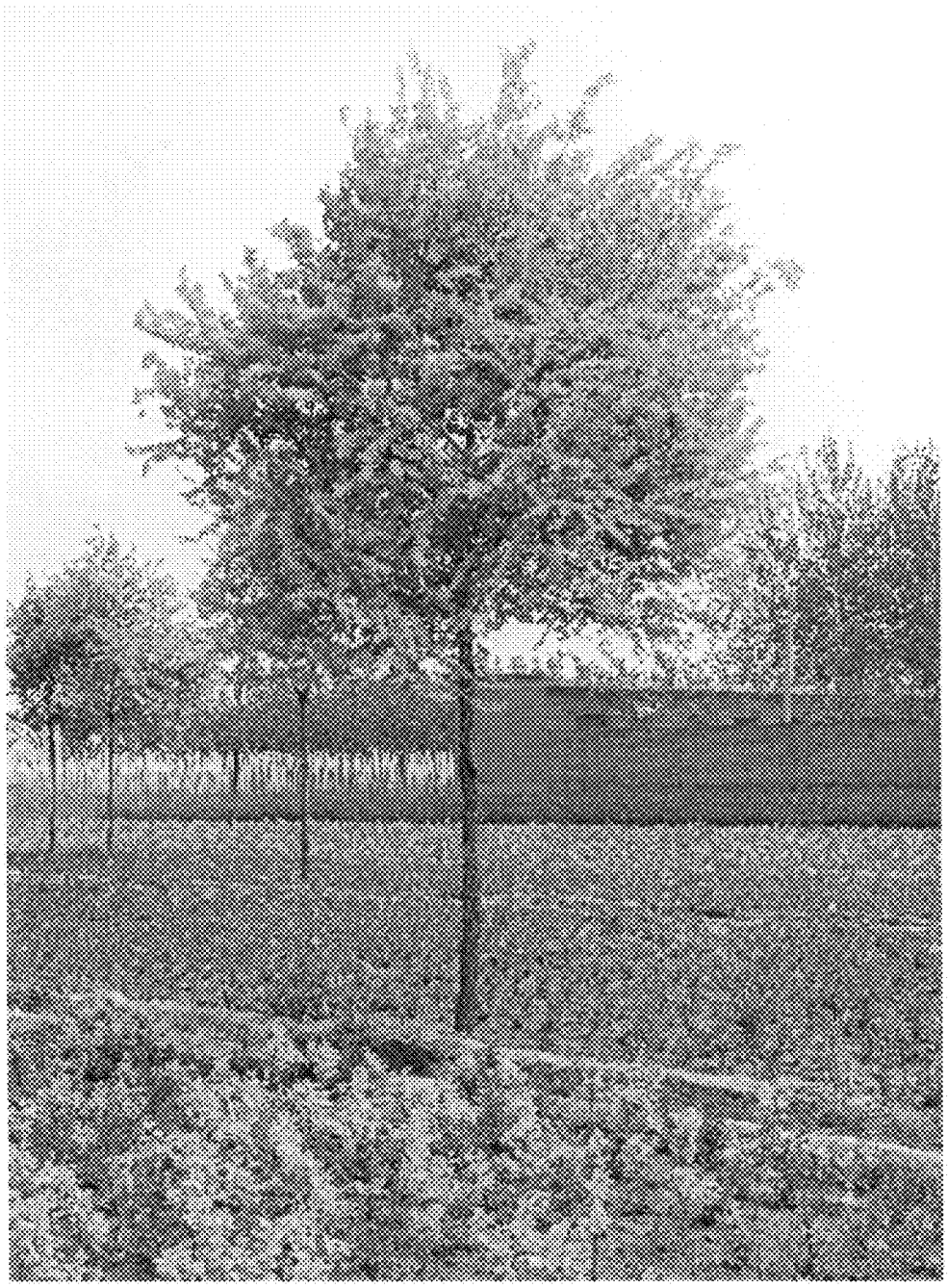
FIG. 1 illustrates the overall plant habit of 'Meirenyu' in early summer.
Figure 2:
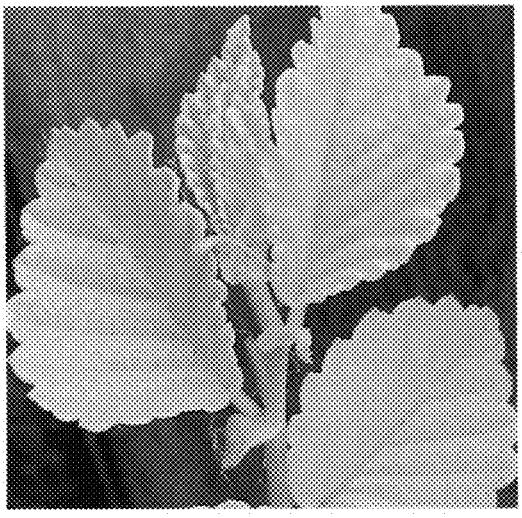
FIG. 2 provides a close-up view of the foliage of 'Meirenyu' in early summer.
Figure 3:
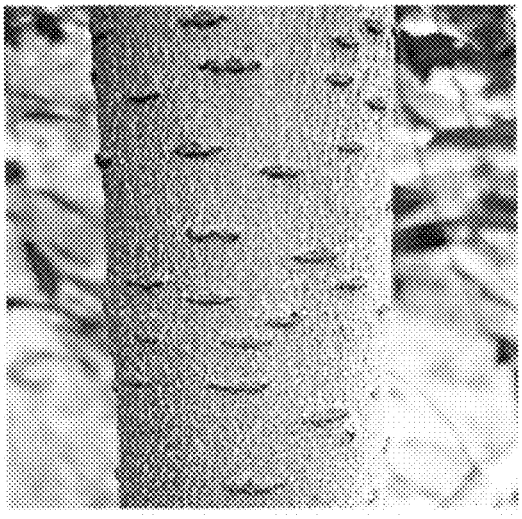
FIG. 3 provides a close-up view of the bark of 'Meirenyu'.
Figure 4:
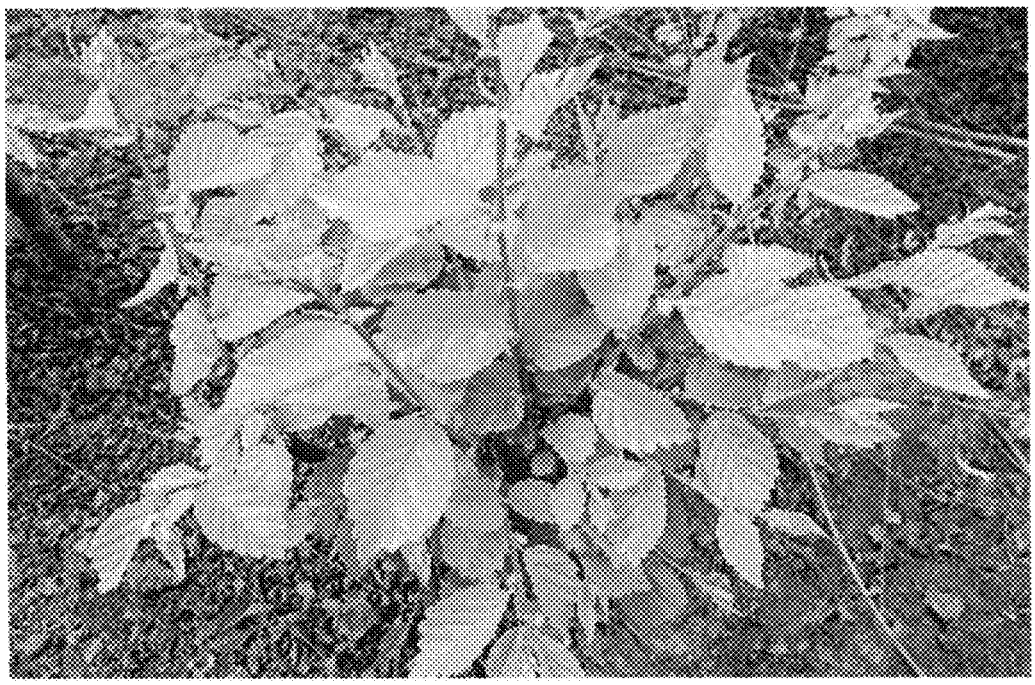
FIG. 4 was taken of a two year-old plant of 'Meirenyu' and provides a view of current years branches.

The colors in the photographs may differ slightly from the color values cited in the detailed botanical description, which accurately describe the colors of the new *Ulmus.*

DETAILED BOTANICAL DESCRIPTION

The following is a description of seven year-old plants of the new cultivar as field grown in Shijiazhuang City, China. The climate in Shijiazhuang City is semi-arid, with hot humid summers, cold, windy, and dry winters and natural light levels of 2,427 hours per year. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant habit.*—Deciduous, upright tree with an elliptic-shaped canopy.

*Height and spread.*—Reaches about 11 m in height and about 5.6 m in width in seven years.

*Cold hardiness.*—At least in U.S.D.A. Zones 3 to 9.

*Diseases and pests.*—No apparent disease problems have been observed to date.

*Environmental conditions.*—Tolerant to poor soils, drought, and moderate salt levels.

*Root description.*—Fibrous, freely branched.

*Propagation.*—Softwood cuttings and grafting.

*Growth rate.*—Vigorous.

Stem description:

*Shape.*—Round to slightly oval.

*Stem color.*—Main trunk and secondary branches (bark) with good sun exposure; 196C, with lenticels (about 0.75 per square centimeters) 166C in color, main trunk and secondary branches (bark) without good sun exposure; 173A.

*Branching.*—About 13 lateral branches with internode length between secondary branches an average of 2.8 cm, branches held at about a 60° angle.

*Stem size.*—Main trunk; an average of 10.2 cm in diameter (from base), secondary branches; an average of 3.5 cm in diameter and 3 m in length, and tertiary branches; an average of 1.6 cm in diameter and 2 m in length.

*Stem surface.*—Young growth smooth with shoot tips pubescent, mature bark has vertical striations and is somewhat glaucous.

Foliage description:

*Leaf shape.*—Elliptic to broadly ovate.

*Leaf division.*—Simple.

*Leaf aspect.*—Upward to horizontally.

*Leaf base.*—Obtuse.

*Leaf apex.*—Acute.

*Leaf fragrance.*—None.

*Leaf venation.*—Pinnate, 7 to 9 pairs per leaf, 154B in color on upper surface, 150D in color on lower surface.

*Leaf margins.*—Double serrate.

*Leaf arrangement.*—Alternate.

*Leaf internode length.*—An average of 3.0 cm.

*Leaf attachment.*—Petiolate.

*Leaf surface.*—Puberulent on upper surface and glabrous on lower surface.

*Leaf size.*—5 to 7 cm in length and 3 to 4 cm in width.

*Leaf color.*—Young leaves; 154A to 154B on upper surface and 150B on lower surface, mature and fall leaves; 149A on upper and lower surface.

*Petioles.*—3 to 4 mm in length and 1 mm in width, 150B in color, surface is pubescent.

Flower description:

*General.*—Typical for the species, characterized as inconspicuous and occurring in late March in Shijiazhuang City, China, flowers are hermaphrodite, appearing in clusters before the leaves on the previous years twigs.

*Inflorescence type.*—Fascicled cymes of 15 to 20 flowers per cyme.

*Inflorescence size.*—About 2 cm in length and up to 1 cm in width.

*Lastingness of inflorescence.*—About 7 days.

*Flower type.*—Bell-shaped.

*Flower size.*—About 3 mm in height and 2 mm in width.

*Flower fragrance.*—None.

*Petals.*—Absent.

*Calyx.*—Bell-shaped, fused, 4-lobed apex.

*Sepals.*—4, fused at base with lobes free toward apex, about 2.5 mm in height and 2 mm in width, apex lobes are about 1 mm in width and height with acute apex, glabrous and smooth on outer and inner surface, 154C in color on fused portion and apex portion 187C on inner and outer surface, margin of lobes ciliate.

*Peduncle.*—About 0.5 mm in length and width, 144D in color, glabrous surface.

*Pedicels.*—None, sessile to peduncle.

Reproductive organs:

*Pistil.*—1, about 2 mm in height and 1 mm in width, 144D in color.

*Stamens.*—3 to 9, filaments are about 3 mm in height and 0.3 mm in width, 69C in color, anthers are about 1 mm in height and width, color 178D and turning when mature to 200C.

*Fruit/seed.*—Typical for species, produced between April to June in Shijiazhuang City, China, fruit is a samara that is dry and rounded and flattened in shape, 1.2 to 2 cm in diameter, forming a broad papery wing encircling the seed, 145B in color with margin 151C.

It is claimed:

1. A new and distinct cultivar of elm tree named 'Meirenyu' as herein illustrated and described.

* * * * *

UNITED STATES PATENT AND TRADEMARK OFFICE

CERTIFICATE OF CORRECTION

PATENT NO. : PP23,756 P2
APPLICATION NO. : 13/374151
DATED : July 23, 2013
INVENTOR(S) : Huang et al.

It is certified that error appears in the above-identified patent and that said Letters Patent is hereby corrected as shown below:

On the title page, item [73]

After Hebei Academy of Forestry Science,
Shijiazhuang (CN)

should read:

Shijiazhuang Lvyuanda Landscape
Architecture Engineering Co.
Shijiazhuang (CN)

Signed and Sealed this
Thirteenth Day of May, 2014

Michelle K. Lee

Michelle K. Lee
*Deputy Director of the United States Patent and Trademark Office*